(12) United States Patent
Guzman Sanchez et al.

(10) Patent No.: US 9,585,693 B2
(45) Date of Patent: Mar. 7, 2017

(54) COMPRESSIVE PLATES FOR THE PLACENTAL INSERTION SITE FOR USE IN CASES OF PLACENTA PREVIA

(71) Applicants: Jose Arnoldo Guzman Sanchez, Jalisco (MX); Eduardo Rodriguez de Anda, Jalisco (MX)

(72) Inventors: Jose Arnoldo Guzman Sanchez, Jalisco (MX); Eduardo Rodriguez de Anda, Jalisco (MX)

( * ) Notice: Subject to any disclaimer, the term of this patent is extended or adjusted under 35 U.S.C. 154(b) by 180 days.

(21) Appl. No.: 14/380,799

(22) PCT Filed: Feb. 18, 2013

(86) PCT No.: PCT/MX2013/000023
§ 371 (c)(1),
(2) Date: Aug. 25, 2014

(87) PCT Pub. No.: WO2013/125935
PCT Pub. Date: Aug. 29, 2013

(65) Prior Publication Data
US 2015/0025542 A1    Jan. 22, 2015

(30) Foreign Application Priority Data
Feb. 23, 2012   (MX) .................. MX/a/2012/002339

(51) Int. Cl.
*A61B 17/42*   (2006.01)
*A61B 17/34*   (2006.01)
*A61B 17/12*   (2006.01)

(52) U.S. Cl.
CPC .............. *A61B 17/42* (2013.01); *A61B 17/34* (2013.01); *A61B 2017/12004* (2013.01); *A61B 2017/4216* (2013.01)

(58) Field of Classification Search
CPC ..... A61B 17/0206; A61B 17/08; A61B 17/12; A61B 17/34; A61B 17/42; A61B 17/122;
(Continued)

(56) References Cited

U.S. PATENT DOCUMENTS 3,575,405 A * 4/1971 Harding .................. B25B 5/106
                                                   269/211
4,555,100 A * 11/1985 Ditto ........................ B25B 5/02
                                                   269/166

(Continued)

FOREIGN PATENT DOCUMENTS

CN           201171696          12/2008

*Primary Examiner* — Melanie Tyson
*Assistant Examiner* — Majid Jamialahmadi
(74) *Attorney, Agent, or Firm* — Defillo & Associates, Inc; Evelyn A Defillo

(57) ABSTRACT

Compressive plates of the placental insertion site for use in cases of placenta previa includes: an axle plate including a primary plate which is fixed, a threaded bar that has machined two plates and a diameter reduction section, a secondary plate having a hole with a diameter and a shape that allows the introduction of the bar, a punch with conical tip, a nut and a locknut, and a protective cover. The punch pierces the front and back walls of the uterus corresponding to the placental insertion site. Then, the secondary plate is introduced that approaches to the primary plate until obtaining enough pressure to stop the bleeding, the nut and locknut are placed, and, finally, the protective cover is screwed.

7 Claims, 4 Drawing Sheets

(58) Field of Classification Search
CPC ...... A61B 17/4241; A61B 2017/00407; A61B 2017/2837; A61B 2017/081; A61B 2017/088; A61B 2017/12004; A61B 2017/4216; A61B 2017/4225; A61B 2017/4233; B25B 5/068; B25B 5/003; B25B 5/006; B25B 5/101; B25B 5/02; B25B 5/166; B25B 5/163; B25B 5/00; B25B 1/00; B25B 1/20; B25B 5/085; Y10T 29/5387; Y10T 29/505; E01B 9/28; F02M 2200/223; F02M 2200/855; B23Q 5/326
USPC ........ 606/185, 184, 119; 269/6, 143, 249, 3, 269/95; 29/255, 278, 270
See application file for complete search history.

(56) References Cited

U.S. PATENT DOCUMENTS

| | | | |
|---|---|---|---|
| 7,673,860 B2* | 3/2010 | Ben-Gigi | B25B 1/103 269/246 |
| 8,978,221 B1* | 3/2015 | Somerville | B25B 27/06 254/93 R |
| 2004/0153097 A1 | 8/2004 | Burbank et al. | |
| 2008/0188863 A1 | 8/2008 | Chu | |
| 2011/0251622 A1 | 10/2011 | Basic et al. | |

* cited by examiner

COMPRESSIVE PLATES FOR THE PLACENTAL INSERTION SITE FOR USE IN CASES OF PLACENTA PREVIA

CROSS REFERENCE TO RELATED APPLICATION

This application is a national stage entry of PCT/MX2013/000023 filed Feb. 18, 2013, under the International Convention claiming priority over Mexican Application No. MX/a/2012/002339 filed Feb. 23, 2012.

TECHNICAL FIELD

The present invention relates to a surgical device that compresses the uterine walls in the corresponding section of the placenta insertion site in cases of placenta previa. This device, once applied, does not allow blood output from the place where the placenta is attached, thus avoiding the profuse bleeding that invariably occurs in placenta previa cases.

This device is essentially comprised of two compressive plates with specific attachments, allowing the compression on the placenta insertion site.

BACKGROUND

There is no specific tool that will compress the uterine walls at the level of the site of the placental insertion when a surgery is performed by placenta previa.

Although there is a tool called Dartigues histerolabo's clamp, FIG. 1, this fails to uniformly compress the uterine walls of the placental insertion site. Also, it cannot be used because its design prevents the surgical manipulation on site where the caesarean section was performed; in addition, both the handle and the oppressive side of the clamp are very small.

Conversely, the proposed invention achieves uniform compression of the placenta insertion site by the external compression of the walls of the female womb. This device also allows to adapt to the dimensions of the patient matrix thickness.

Since this device has been used, there has been a decrease of at least 80% in the bleeding that occurred at the placenta insertion site.

Problem to Solve:

To reduce maternal death by bleeding. The World Health Organization points out that maternal bleeding is the leading cause of maternal death in Latin America, which is a tragedy.

The World Health Organization's fifth objective literally states, "maternal death should be reduced"; a goal that must be attained.

How to Solve the Problem:

The bleeding problem, of which we refer to, has been solved by using the aforementioned compressive plates. These completely block the maternal blood flow to the placenta.

The experience with 70 surgeries completed in which the compressive plates of the placental insertion site was applied to be used in cases of placenta previa, which proposes the present invention, demonstrates the usefulness of this device in function that has reduced at least 80% of the torrential bleeding that occurred with placenta previa.

DETAILED DESCRIPTION

The present invention proposes compressive plates for the placental insertion site to be used in placenta previa cases; this device comprises five parts, which are as follows:

1. First plate, see FIG. 2.
2. Second plate, see FIG. 3.
3. Punch, see FIG. 4.
4. Nut and locknut, see FIG. 5.
5. Cover, see FIG. 6.

FIG. 2 shows the first plate (2.1) having a rectangular shape, to which a cylindrical threaded bar (2.2) is placed perpendicular to the first plate. The distal end of the threaded bar has a diameter reduction section (2.3) having threads. On this diameter reduction section (2.3), the punch is attached, see FIG. 4, or the cover, see FIG. 6. The bar (2.2) has machined a couple of flat sections (2.4) diametrically opposed, along the entire length of the bar (2.2). Also the diameter reduction section (2.3) may have other attachment mechanisms different from threading, such as elements of pressure inclusion, mechanical or magnetic locks, etc.

2. Second plate, see FIG. 3. The second plate (3.1) has the same shape and dimension of the first plate (2.1); in the center of this plate is a machined hole (3.2) that is not completely round, because it has two parallel sides, in such a way to allow the second plate introduction (3.1) on the bar (2.2) to coincide the pair of flat sections (2.4) with the two parallel sides of the hole (3.2), in order to prevent the rotation of the second plate (3.1).

The machining of the flat sections (2.4) and the parallel sides of the hole (3.2) are with an orientation that ensures that the larger face of the first plate (2.1) is allowed to coincide in its entirety with the larger face of the second plate (3.1).

In addition, the flat sections (2.4) may have other geometries that prevent the rotation of the second plate (3.1), such as a longitudinal slot, a single flat face, non-parallel plates, etc. In addition, the geometric shape of primary plate (2.1) and the secondary plate (3.1) may be different from the rectangular.

Punch, see FIG. 4. The punch is the element that allows the perforation of the front and back walls of the feminine matrix since it has a machining end with a termination of a conical tip (4.1). At the other end it has a threaded hole (4.2) that allows to be screwed in the diameter reduction section (2.3) of the bar (2.2).

Similarly, the conical end (4.1) can be replaced with a pyramidal tip.

Nut and locknut, see FIG. 5. The nut (5.1) is the first element which is screwed on to the bar (2.2) causing a progressive approximation between the first plate (2.1) and the second plate (3.1). The locknut (5.2) has the function only to ensure the positioning of the nut (5.1). Also the nut (5.1) and the locknut (5.2) may have geometry other than circular, such as square, pentagonal, hexagonal, or one with a larger number of faces with rounded corners.

Cover, see FIG. 6. It is a cylinder having at one end semispherical finishing (6.1); at the other end has an internal threaded (6.2) that when screwed in the part called the diameter reduction section (2.3) protects the intra-abdominal organs.

Also the cover, FIG. 6, may be replaced by a threaded sphere or any other protective element that covers the section called diameter reduction.

In addition, the surface of the different components of compressive plates of the placental insertion site, to be used in cases of placenta previa, may have a finished anti-skid surface, which allows a better grip and manipulation of the parts.

Operative sequence of the compressive plates in placental insertion site for use in placenta previa cases.

In the axle plate, FIG. 2, the punch is screwed, FIG. 4, in the part known as the diameter reduction section (2.3).

Then both walls of the uterus are perforated, in the corresponding placental insertion site.

Without removing the axle plate, FIG. 2, of the uterus, the punch is unscrewed, FIG. 4, and the second plate (3.1) is placed, aligning the hole (3.2) with the bar (2.2).

Approximating to the maximum, manually, the first plate (2.1) to the second plate (3.1) to compress the placental insertion site, and the plates are secured by placing the nut (5.1). The pressure between the plates may be increased by further turning of the nut (5.1).

The locknut (5.2) is threaded on the bar (2.2) until making contact with the nut (5.1) in order to secure its position.

Covering with the cover, FIG. 6, the part known as the diameter reduction (2.3).

The Assembly of the total number of parts that constitute the compressive plates of placental insertion site for use in cases of placenta previa is shown in FIG. 7.

Figure 1:
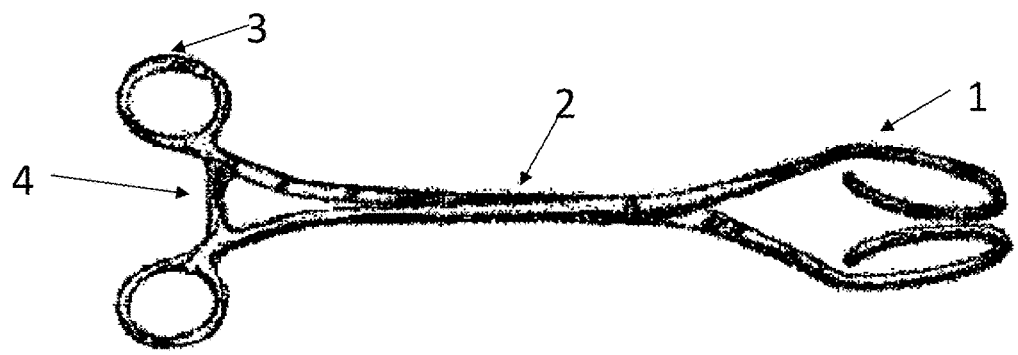
FIG. 1: Dartigues histerolabo's clamp: This clamp has the following characteristics: Part (1): Clamp tip; characterized by having two compressive ellipsoidal shape elements in each one of the arms. Part (2): Axis of rotation; allowing the opening or closing of the clamp arms. Part (3): Clamping rings and control of the opening or closing of the clamp arms. Part (4): Fastening slots and pressure adjustment of the clamp tip.
Figure 2:
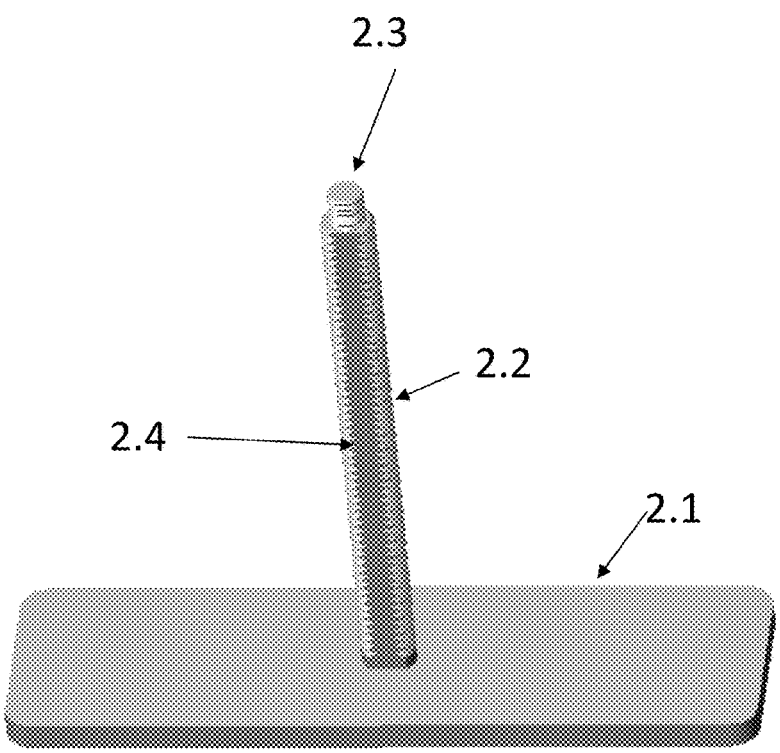
FIG. 2: First plate.
Figure 3:
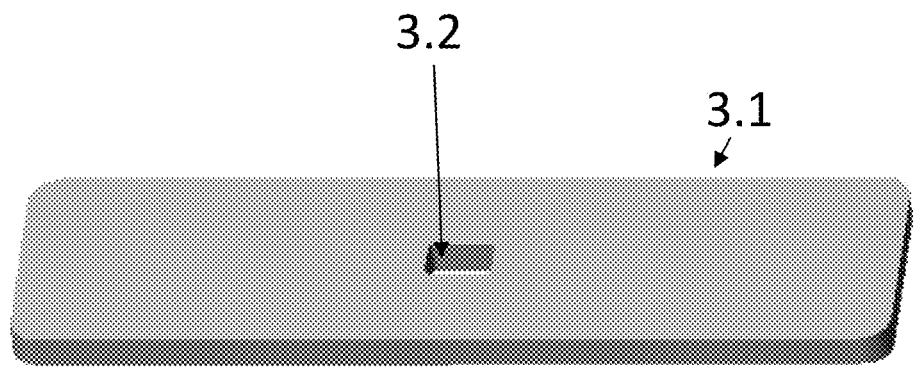
FIG. 3: Second plate.
Figure 4:
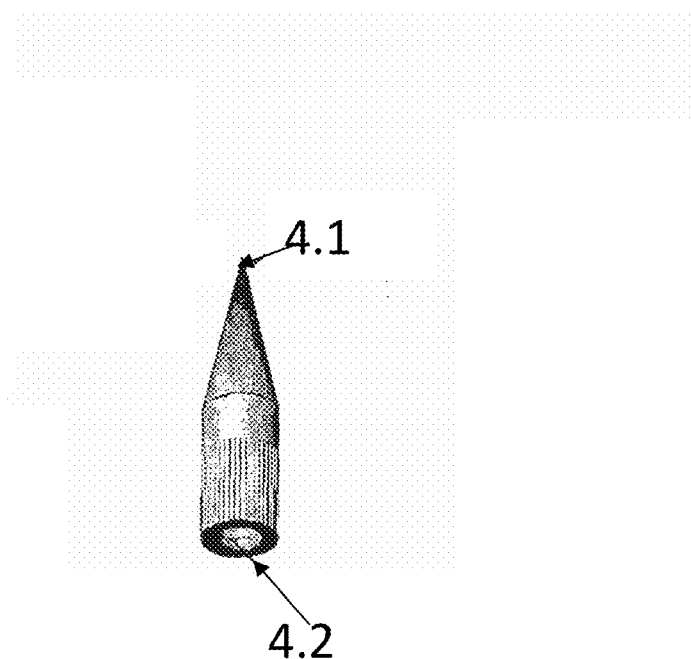
FIG. 4: Punch.
Figure 5:
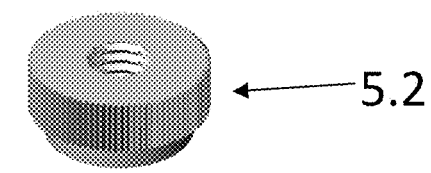
FIG. 5: Nut and locknut.
Figure 5:
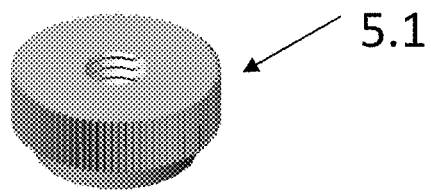
Figure 6:
FIG. 6: Cover.
Figure 7:
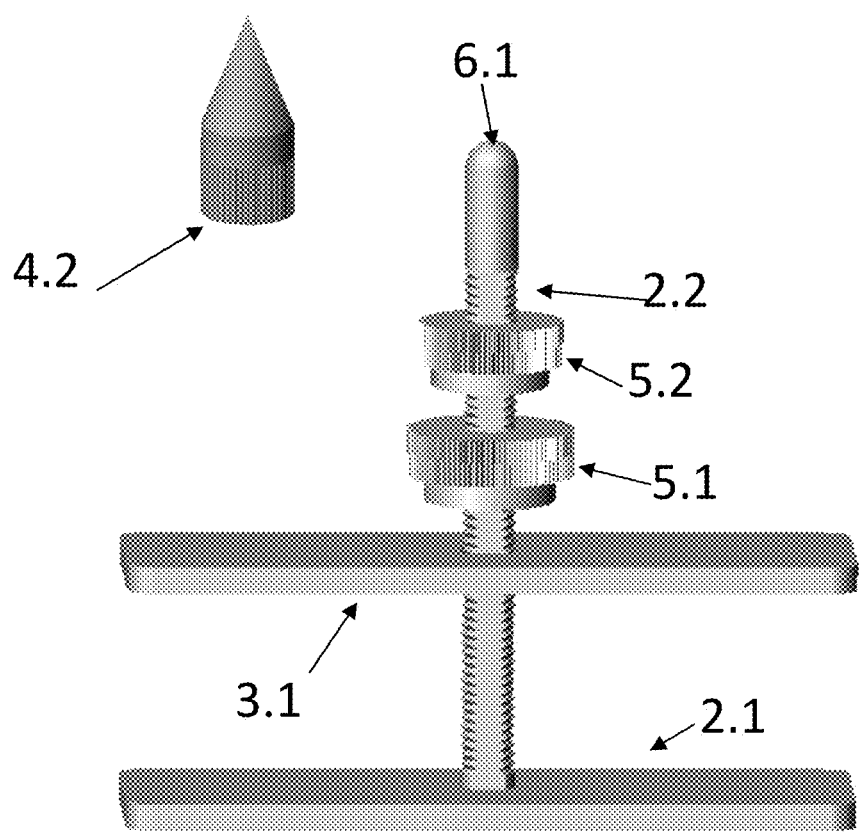
FIG. 7: Assembly of total number of pieces that constitute the compressive plates of the placental insertion site to be used in cases of placenta previa.

The claims are based on the fundamental problem of bleeding in placenta previa, which is a serious complication that occurs during a caesarean section, to which the present device offers an alternative solution that has the experience of 70 surgeries practiced in Fray Antonio Alcalde Civil Hospital of Guadalajara, Jalisco.

Having described my invention, as above, I consider it as a novelty and claim my property in the following claims.

The invention claimed is:

1. Compressive plates of a placental insertion site for use in cases of a placenta previa comprising:
a first flat plate (2.1) including a threaded bar (2.2) connected perpendicular to the first flat plate (2.1), the threaded bar (2.2) includes at least one flat section machined into an entire length of a wall of the threaded bar (2.2), and a diameter reduction section (2.3), the diameter reduction section is located at an end of the threaded bar opposite to the primary first flat plate (2.1), the diameter reduction section forms a step with the threaded bar (2.2);
a second flat plate (3.1) placed in parallel with respect to the first flat plate, the second flat plate including a hole (3.2) having a non-rounded shape with two parallel walls, the flat section (2.4) is inserted into the hole (3.2) to prevent the rotation of the second flat plate (3.1);
a punch having a first end including a conical tip (4.1) and a second end including a threaded hole (4.2) that is secured to the diameter reduction section (2.3);
a nut (5.1); and
a locknut (5.2); the nut (5.1) is secured to the threaded bar (2.2) and the locknut (5.2) locks the nut in position
the compressive plates are designed to be inserted into the placenta insertion site to compress the placenta insertion site.

2. The compressive plates according to claim 1, wherein the diameter reduction section includes a clamping mechanisms selected from the group consisting of threads, pressure clamping devices, mechanical locks, and magnetic locks.

3. The compressive plates according to claim 1, wherein the conical tip has a shape of a pyramidal tip.

4. The compressive plates according to claim 1, wherein the nut (5.1) and the locknut (5.2) have a shape selected from the group consisting of circular, square, pentagonal, hexagonal.

5. The compressive plates according to claim 1, wherein the first flat plate (2.1), the threaded bar (2.2), the at least one flat section (2.4), the diameter reduction section (2.3), the second flat plate (3.1), the punch, the conical tip (4.1), the nut (5.1), and the locknut (5.2) has an anti-skid surface.

6. The compressive plates according to claim 1, further including a cover having a cylindrical shape with a first end having a semi-spherical shape (6.1) and a second end including internal threads (6.2), the second end of the cover is secured to the diameter reduction section (2.3).

7. Compressive plates of a placental insertion site for use in cases of a placenta previa comprising:
a first flat plate (2.1) including a threaded bar (2.2) connected perpendicular to the first flat plate, the threaded bar (2.2) includes at least one flat section (2.4) machined into an entire length of a wall of the threaded bar (2.2), and a diameter reduction section (2.3), the diameter reduction section is located at an end of the threaded bar opposite to the primary first flat plate (2.1), the diameter reduction section forms a step with the threaded bar (2.2);
a second flat plate (3.1) placed in parallel with respect to the first flat plate, the second flat plate including a hole (3.2) having a non-rounded shape with two parallel walls, the flat section (2.4) is inserted into the hole (3.2) to prevent the rotation of the second flat plate (3.1);
a punch having a first end including a conical tip (4.1) and a second end including a threaded hole (4.2) that is secured to the diameter reduction section (2.3);
a nut (5.1); and
a locknut (5.2); the nut (5.1) is secured to the threaded bar (2.2) and the locknut (5.2) locks the nut in position;
the compressive plates are designed to be inserted into the placenta insertion site to compress the placenta insertion site;
the first flat plate has the same shape and dimensions as the second flat plate.

* * * * *